US008617125B2

(12) United States Patent
Christiansen

(10) Patent No.: US 8,617,125 B2
(45) Date of Patent: Dec. 31, 2013

(54) MEDICAL DELIVERY SYSTEM COMPRISING A CONTAINER AND A DOSING ASSEMBLY WITH RADIALLY MOVING FASTENING MEANS

(75) Inventor: Asger Voss Christiansen, Guldborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 576 days.

(21) Appl. No.: 12/517,896

(22) PCT Filed: Dec. 15, 2007

(86) PCT No.: PCT/EP2007/064013
§ 371 (c)(1),
(2), (4) Date: Sep. 3, 2009

(87) PCT Pub. No.: WO2008/071804
PCT Pub. Date: Jun. 19, 2008

(65) Prior Publication Data
US 2010/0324498 A1     Dec. 23, 2010

Related U.S. Application Data

(60) Provisional application No. 60/897,079, filed on Jan. 24, 2007.

(30) Foreign Application Priority Data

Dec. 15, 2006 (EP) .................................. 06026029

(51) Int. Cl.
*A61M 5/00* (2006.01)
*A61M 5/315* (2006.01)
*B65D 79/00* (2006.01)

(52) U.S. Cl.
USPC ............ 604/211; 206/527; 206/828; 604/218

(58) Field of Classification Search
USPC ......... 604/110, 186, 187, 188, 192, 195, 196, 604/221, 207–211, 232
See application file for complete search history.

(56) References Cited

U.S. PATENT DOCUMENTS

| RE31,878 E | 4/1861 | Downer |
|---|---|---|
| 1,594,493 A | 8/1926 | Brown |

(Continued)

FOREIGN PATENT DOCUMENTS

| CH | 0315980 | 9/1956 |
|---|---|---|
| CI | 0110501411 | 1/1971 |

(Continued)

OTHER PUBLICATIONS

Novo Nordisk Product Brochure for Insuject-X 1987.

(Continued)

*Primary Examiner* — Kevin C Sirmons
*Assistant Examiner* — William Carpenter
(74) *Attorney, Agent, or Firm* — Wesley A. Nicolas; Marc A. Began; Reza Green

(57) ABSTRACT

A medical delivery system wherein one of a container and a dosing assembly comprises a first fastening means (116) and the other one of the container and the dosing assembly comprises a second fastening means (114); and wherein the second fastening means is adapted to move at least a part of the first fastening means in a radial direction upon rotation of the container in a first rotational direction relative to the dosing assembly, whereby the first and second fastening means engage such that the container and the dosing assembly are locked for relative translational movement. A container and a dosing assembly for use in the medical delivery system.

9 Claims, 5 Drawing Sheets

(56) References Cited

U.S. PATENT DOCUMENTS

| | | | |
|---|---|---|---|
| 2,020,828 A | 11/1935 | Goldberg | |
| 2,707,466 A | 5/1955 | Hoskins | |
| 2,818,864 A | 1/1958 | Hudson | |
| 2,865,372 A | 12/1958 | Miskel et al. | |
| 2,880,723 A | 4/1959 | Adams | |
| 2,888,924 A | 6/1959 | Dunmire | |
| 3,021,840 A | 2/1962 | Hallamore et al. | |
| 3,130,724 A | 4/1964 | Higgins et al. | |
| 3,130,742 A | 4/1964 | Higgins et al. | |
| 3,170,667 A | 2/1965 | Szohatzky | |
| 3,336,924 A | 8/1967 | Sarnoff et al. | |
| 3,375,825 A | 4/1968 | Keller | |
| 3,820,652 A | 6/1974 | Tiiackston | |
| 3,831,599 A | 8/1974 | Needham | |
| 3,895,633 A | 7/1975 | Bartner et al. | |
| 3,916,893 A | 11/1975 | De Felice | |
| 3,989,044 A | 11/1976 | Meierhoefer | |
| 4,089,432 A | 5/1978 | Crankshaw | |
| 4,150,673 A | 4/1979 | Watt | |
| 4,280,723 A | 7/1981 | Moldestad | |
| 4,490,142 A | 12/1984 | Silvern | |
| RE31,873 E | 4/1985 | Howes | |
| 4,592,745 A | 6/1986 | Rex et al. | |
| 4,619,640 A | 10/1986 | Potolsky et al. | |
| 4,619,651 A | 10/1986 | Kopfer et al. | |
| 4,664,656 A | 5/1987 | Taddei | |
| 4,685,314 A | 8/1987 | Greenwalt | |
| 4,693,833 A | 9/1987 | Toshikuni et al. | |
| 4,710,178 A * | 12/1987 | Henri et al. | 604/209 |
| 4,740,205 A | 4/1988 | Seltzer | |
| 4,768,568 A | 9/1988 | Fournier et al. | |
| 4,781,701 A | 11/1988 | Geprags | |
| 4,944,736 A | 7/1990 | Holtz | |
| 4,948,000 A | 8/1990 | Grabenkort | |
| 4,973,318 A | 11/1990 | Holm et al. | |
| 4,976,701 A | 12/1990 | Ejlersen et al. | |
| 5,000,744 A | 3/1991 | Hoffman et al. | |
| 5,002,537 A | 3/1991 | Hoffman et al. | |
| 5,017,190 A | 5/1991 | Simon et al. | |
| 5,084,017 A | 1/1992 | Maffetone | |
| 5,205,833 A | 4/1993 | Harsh et al. | |
| 5,226,896 A | 7/1993 | Harris | |
| 5,244,465 A * | 9/1993 | Michel | 604/208 |
| 5,269,317 A | 12/1993 | Bennett | |
| 5,279,585 A * | 1/1994 | Balkwill | 604/207 |
| 5,286,258 A | 2/1994 | Haber et al. | |
| 5,458,580 A | 10/1995 | Hajishoreh | |
| 5,478,323 A | 12/1995 | Westwood et al. | |
| 5,498,253 A | 3/1996 | Aswad et al. | |
| 5,554,134 A | 9/1996 | Bonnichsen | |
| 5,584,815 A | 12/1996 | Pawelka et al. | |
| 5,611,783 A | 3/1997 | Mikkelsen | |
| 5,688,251 A * | 11/1997 | Chanoch | 604/208 |
| 5,693,027 A | 12/1997 | Hansen et al. | |
| 5,743,889 A | 4/1998 | Sams | |
| 5,938,642 A * | 8/1999 | Burroughs et al. | 604/208 |
| 5,954,700 A | 9/1999 | Kovelman | |
| 5,957,896 A * | 9/1999 | Bendek et al. | 604/207 |
| 6,017,330 A | 1/2000 | Hitchins et al. | |
| 6,197,040 B1 | 3/2001 | LeVaughn et al. | |
| 6,221,046 B1 | 4/2001 | Burroughs et al. | |
| 6,582,399 B1 | 6/2003 | Smith et al. | |
| 6,582,408 B1 | 6/2003 | Buch-Rasmussen et al. | |
| 6,648,859 B2 * | 11/2003 | Bitdinger et al. | 604/232 |
| 7,195,616 B2 | 3/2007 | Diller et al. | |
| 7,513,889 B2 | 4/2009 | Jost | |
| 7,604,619 B2 | 10/2009 | Eich et al. | |
| 2001/0047153 A1 | 11/2001 | Trocki et al. | |
| 2002/0016571 A1 | 2/2002 | Kirchhofer | |
| 2002/0052578 A1 | 5/2002 | Moller | |
| 2002/0099360 A1 | 7/2002 | Bierman | |
| 2002/0169470 A1 | 11/2002 | Kuhr et al. | |
| 2003/0004466 A1 | 1/2003 | Bitdinger et al. | |
| 2003/0078195 A1 | 4/2003 | Kristensen et al. | |
| 2004/0210199 A1 * | 10/2004 | Atterbury et al. | 604/224 |
| 2004/0215152 A1 * | 10/2004 | Kirchhofer et al. | 604/211 |
| 2004/0236285 A1 * | 11/2004 | Fisher et al. | 604/207 |
| 2004/0238776 A1 | 12/2004 | Peters et al. | |
| 2005/0273079 A1 * | 12/2005 | Hohlfelder et al. | 604/890.1 |
| 2006/0153693 A1 | 7/2006 | Fiechter et al. | |
| 2008/0051713 A1 | 2/2008 | Kohlbrenner | |
| 2008/0221530 A1 | 9/2008 | Glejbol et al. | |
| 2008/0234634 A1 | 9/2008 | Eiland et al. | |
| 2008/0243087 A1 | 10/2008 | Enggaard et al. | |
| 2009/0043264 A1 | 2/2009 | Glejbol et al. | |
| 2009/0259197 A1 | 10/2009 | Christiansen | |
| 2009/0281505 A1 | 11/2009 | Hansen et al. | |
| 2009/0312717 A1 | 12/2009 | Christiansen | |
| 2010/0010455 A1 | 1/2010 | Elahi et al. | |
| 2010/0016806 A1 | 1/2010 | Glejbol et al. | |
| 2010/0030158 A1 | 2/2010 | Christiansen | |
| 2010/0042054 A1 | 2/2010 | Elahi et al. | |
| 2010/0114025 A1 | 5/2010 | Moller | |
| 2011/0046566 A1 | 2/2011 | Elahi et al. | |

FOREIGN PATENT DOCUMENTS

| | | |
|---|---|---|
| DE | 2137405 | 2/1973 |
| DE | 44 19 235 | 12/1995 |
| DE | 20110690 | 9/2001 |
| EP | 217055 | 4/1987 |
| EP | 549 694 | 7/1993 |
| EP | 762311 | 3/1997 |
| EP | 774270 | 5/1997 |
| EP | 897728 | 2/1999 |
| EP | 897729 | 2/1999 |
| EP | 897728 | 5/2003 |
| GB | 301961 | 12/1928 |
| GB | 1205201 | 9/1970 |
| GB | 1437595 | 5/1976 |
| GB | 1525455 | 9/1978 |
| GB | 2 214 819 | 9/1989 |
| JP | 11-276583 A | 10/1999 |
| JP | 2002509469 A | 3/2002 |
| JP | 2002520098 A | 7/2002 |
| WO | WO 89/02760 | 4/1989 |
| WO | WO 90/09202 | 8/1990 |
| WO | WO 92/04926 | 4/1992 |
| WO | WO 98/47559 | 10/1998 |
| WO | WO 98/56438 | 12/1998 |
| WO | WO 00/02605 | 1/2000 |
| WO | WO 2000/35519 | 6/2000 |
| WO | WO 01/72361 | 10/2001 |
| WO | WO 02/30490 | 4/2002 |
| WO | WO 03/011372 | 2/2003 |
| WO | WO 03/011373 | 2/2003 |
| WO | WO 03/017915 | 3/2003 |
| WO | WO 2006/069456 | 7/2006 |
| WO | WO 2008/009646 | 1/2008 |

OTHER PUBLICATIONS

Non-Final Office Action mailed Apr. 9, 2004 in U.S. Appl. No. 10/230,428, filed August 23, 2002; First Named Inventor: Kristensen.

Non-Final Office Action mailed Nov. 18, 2004 in U.S. Appl. No. 10/230,428, filed Aug. 23, 2002; First Named Inventor: Kristensen.

Notice of Allowance mailed May 19, 2005 in U.S. Appl. No. 10/230,428, filed Aug. 23, 2002; First Named Inventor: Kristensen.

Non-Final Office Action mailed Feb. 9, 2006 in U.S. Appl. No. 10/230,428, filed Aug. 23, 2002; First Named Inventor: Kristensen.

Notice of Allowance mailed Oct. 10, 2006 in U.S. Appl. No. 10/230,428, filed August 23, 2002; First Named Inventor: Kristensen.

Non-Final Office Action mailed Dec. 12, 2006 in U.S. Appl. No. 10/230,428, filed Aug. 23, 2002; First Named Inventor: Kristensen.

Non-Final Office Action mailed Feb. 10, 2009 in U.S. Appl. No. 11/784,738, filed Apr. 9, 2007; First Named Inventor Kristensen.

Final Office Action Mailed Jun. 2, 2009 in U.S. Appl. No. 11/784,738, filed Apr. 9, 2007; First Named Inventor Kristensen.

Final Office Action mailed Aug. 12, 2010 in U.S. Appl. No. 12/522,566, filed Sep. 2, 2009; First Named Inventor: Kristensen.

Notice of Allowance mailed Dec. 13, 2010 in U.S. Appl. No. 12/522,566, filed Sep. 2, 2009; First Named Inventor: Kristensen.

(56) References Cited

OTHER PUBLICATIONS

Non-Final Office Action mailed Oct. 29, 2010 in U.S. Appl. No. 12/305,684, filed Dec. 19, 2008; First Named Inventor: Steenfeldt-Jensen.
Non-Final Office Action mailed Jan. 19, 2010 in U.S. Appl. No. 12/373,339, filed Jan. 12, 2009 by Hansen.
Final Action mailed Jul. 30, 2010 in U.S. Appl. No. 12/373,339, filed Jan. 12, 2009 by Hansen.
Non-Final Office Action mailed Nov. 24, 2010 in U.S. Appl. No. 12/373,339, filed Jan. 12, 2009 by Hansen.
Non-Final Office Action Mailed February 18, 2011 in U.S. App. No. 12/373,340 Filed January 12, 2009 by Christiansen.
Non-Final Office Action mailed Feb. 17, 2011 in U.S. Appl. No. 12/357,013, filed Jan. 21, 2009 by Christiansen.
Non-Final Office Action Mailed Feb. 1, 2010 in U.S. Appl. No. 12/374,600, filed Jan. 21, 2009 by Christiansen.
Final Office Action mailed Jul. 15, 2010 in U.S. Appl. No. 12/374,600, filed Jan. 21, 2009 by Christiansen.
Non-Final Office Action mailed Mar. 4, 2011 in U.S. Appl. No. 12/374,600, filed Jan. 21, 2009 by Christiansen.
English language machine translation of CH0315980.
English language machine translation of CH0501411.
English language machine translation of DE20110690.
English language machine translation of DE2137405.
English language machine translation of DE4419235.
Search Report from International Application No. PCT/EP2007/062661, mailed Feb. 25, 2008.

* cited by examiner

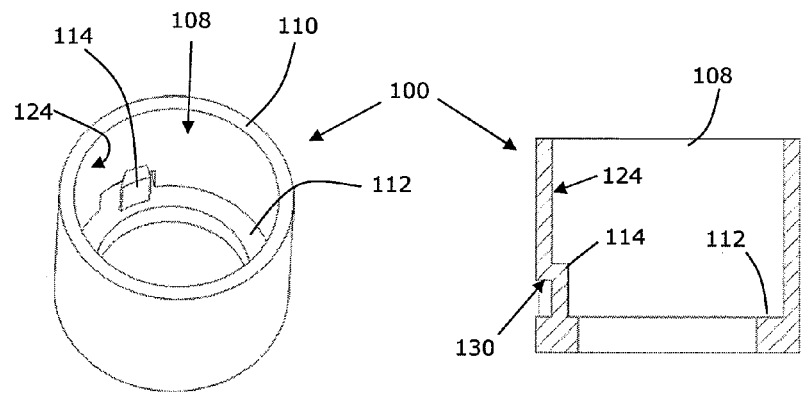
Fig. 1
Fig. 2
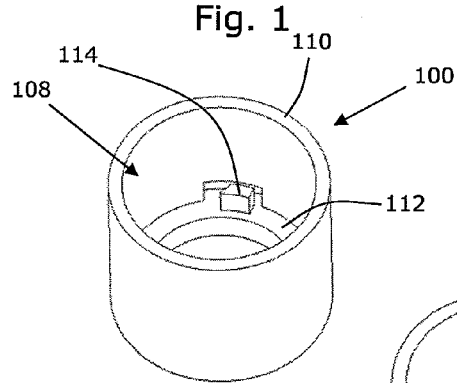
Fig. 3a
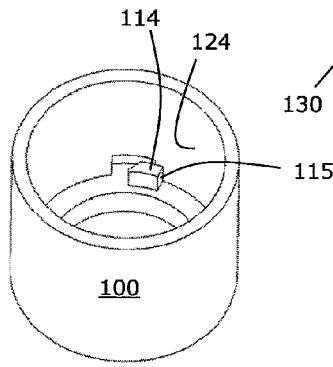
Fig. 3b
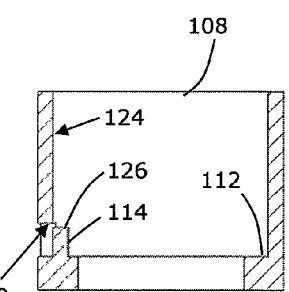
Fig. 4
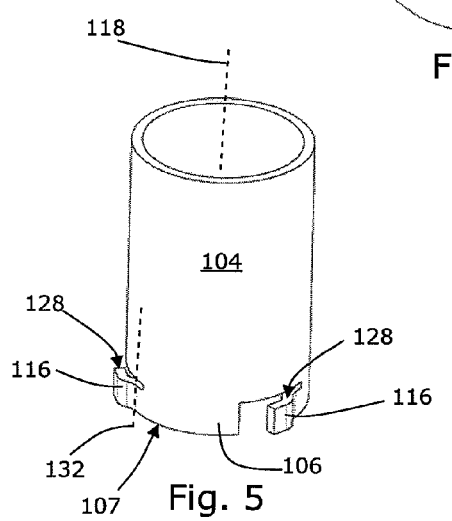
Fig. 5
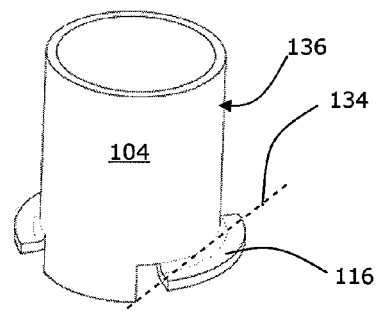
Fig. 6

MEDICAL DELIVERY SYSTEM COMPRISING A CONTAINER AND A DOSING ASSEMBLY WITH RADIALLY MOVING FASTENING MEANS

CROSS-REFERENCE TO RELATED APPLICATIONS

This application is a 35 U.S.C. §371 national stage application of International Patent Application PCT/EP2007/ 064013 (published as WO 2008/071804), filed Dec. 15, 2007, which claimed priority of European Patent Application 06026029.6, filed Dec. 15, 2006; this application further claims priority under 35 U.S.C. §119 of U.S. Provisional Application 60/897,079, filed Jan. 24, 2007.

The present invention relates to a medical delivery system comprising a container adapted to be fastened to a dosing assembly. In particular the present invention relates to a medical delivery system having a first and a second fastening means for fastening the container to the dosing assembly. Moreover, the present invention relates to a container for use in the medical delivery system. Additionally, the present invention relates to a dosing assembly for use in the medical delivery system.

BACKGROUND OF THE INVENTION

Generally, in order to provide superior medication delivery devices which are likely to be well received by particular groups of patients, a greater diversity in drug delivery systems have been launched to the benefit of patients. As the number of commercially available delivery systems increase, numerous different types of medication holding cartridges or containers are distributed. Most of these types of containers differ in various aspects.

Each medicament container may be filled with a particular type of medicament selected from a large variety of different medicaments, but also different kinds of the same class of medicament (e.g. rapid or long acting insulin) and different concentrations of each particular medicament may be accommodated in the containers.

Moreover, different container volumes may be introduced in order to customize each container, and, thus, the delivery system to the needs of particular users. Variation of container volume may be provided by changing the length or diameter of the container. These modifications usually imply corresponding modifications of the dosing assembly of a medication delivery system, so as to provide a particular stroke of a driving element for expelling the medicament from the container or to provide optimal dosing precision. Further discrimination between different medicament containers may be occasioned by the design requirements for each particular delivery system, such as required sliding friction of the piston accommodated in the container.

In order to discriminate between a larger variety of available containers, numerous container coding and coupling systems have been developed. The following mechanical coding and coupling systems are known in the art:

U.S. Pat. No. 5,611,783 relates to a pen shaped syringe comprising a distal part which may comprise an ampoule and a proximal part containing a dose setting and drive mechanism. The proximal and distal parts have interlocking bayonet coupling means. Protrusions may be provided to form a pattern ensuring that a certain distal part may only be used in connection with a certain proximal part.

WO 03/017915 A1 discloses a cartridge having a distal end provided with a mechanical coding. The mechanical coding has the form of a circular protrusion where the circular outer diameter is dedicated a specific concentration of insulin contained in the cartridge.

U.S. Pat. No. 5,693,027 discloses a plastic top for adapting a standard cartridge to a chosen syringe. The plastic top may be provided with means for keyed engagement with corresponding means in a syringe to keep it unrotatable when mounted with a cartridge in the syringe. In some types of syringes such keyed engagement between cartridge and syringe is further used to ensure that only a certain type of cartridge is used.

Yet another prior art system is described in DE 201 10 690.

U.S. Pat. No. 6,648,859 B2 discloses a drug cartridge assembly for use with a reusable pen body assembly of a medication delivery pen. In order to eliminate cross-use the pen body assembly and the drug cartridge are keyed i.e. they may be threadedly engaged by corresponding threads and grooves, bayonet threads, and grooves, snap fits or a pair of lugs that mate in reverse Luer-Lock manner. The mating members are selected so as to prevent cross-use with other assemblies, e.g., the pitch of the threads may be angled so as to mate only with one another and not with other assemblies.

US Patent application No. 2001 0047153 further describes an embodiment of a syringe/injector interface where the injector includes a collet member which is adapted to rotate with respect to the injector during coupling and uncoupling of the syringe and wherein the collet member includes a plurality of flexible segmented members arranged to move radially during coupling/uncoupling. This solution provides a somewhat complex design and is rather inefficient with respect to the volume that is required for the interface components.

It is an object of a preferred embodiment of the present invention to provide an alternative to the known systems. Furthermore, it is an object of a preferred embodiment of the present invention to provide a medication delivery system with a large number of possible coding geometries.

Furthermore, it is an object of a preferred embodiment of the present invention to provide a coding system wherein the user experiences substantially the same operational fastening/coupling/locking movement when the container and dosing assembly of a predetermined medical delivery system are coupled/uncoupled (locked/unlocked) to each other regardless of the specific choice among sets of compatible container/dosing assemblies.

Furthermore, it is an object of a preferred embodiment of the present invention to provide an intuitive and simple fastening mechanism for fastening the container to the dosing assembly.

BRIEF DESCRIPTION OF THE INVENTION

In a FIRST aspect the present invention relates to a medical delivery system comprising:
- a container adapted to contain a medicament in a chamber defined by the container and a slidably arranged piston (not shown) which is moveable in a distal direction towards an outlet (not shown) so as to reduce the volume of the chamber and expel the medicament through the outlet;
- a dosing assembly adapted to be fastened to the container, so as to allow a driver (not shown) of the dosing assembly to move the piston of the container in the distal direction;

wherein one of the container and the dosing assembly defines a first part comprising a first fastening means and the other one of the container and the dosing assembly defines a second part comprising a second fastening means, the first and the second fastening means being adapted to fasten said first part to the second part by translationally moving the first part relative to the second part along an axis followed by a relative rotational locking movement around the axis;

wherein the first fastening means is radially moveable from an initial non-locking position into a second locking position, the first fastening means further defining a first locking surface adapted to engage a second locking surface formed in the second part when the first fastening means is in its second locking position whereby the first part is axially retained with respect to the second part; and wherein, responsive to said relative rotational locking movement, the first fastening means rotates relative to the second fastening means, the second fastening means being adapted to urge the first fastening means into its second locking position upon relative rotational movement between the first fastening means and the second fastening means.

In the context of the present invention the term "medical delivery system" shall be understood as any system capable of administering a medicament-containing flowable drug.

Examples of medical delivery systems are infusion pump applications, dosers, pen-shaped dosers, motor-dosers, and automated syringes such as the AutoPen™.

The invention is applicable to all kinds of medicament delivery devices capable of delivering a medicament to a user from a container which is adapted to be coupled to a dosing assembly of the delivery device. The delivery device may include any delivery device for transcutaneous, subcutaneous, intravenous, intra muscular or pulmonary administration of a drug.

As used herein, the term "medicament" is meant to encompass any medicament-containing flowable drug capable of being passed through a delivery means such as a hollow needle in a controlled manner, such as a liquid, solution, gel or fine suspension. Representative medicaments includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

The chamber of the container may be defined by one or more sidewalls of the container and the slidably arranged piston. In most embodiments at least a part of the container is ring-shaped (has a ring-shaped cross-section) and defines a cylindrical cavity in which the piston is received. The distal end of the container may comprise a seal for penetration by a cannula so as to allow a medicament contained in the chamber to be expelled through the cannula. The distal end of the container may be adapted to be attached to a holder holding a cannula. As an example the distal end of the container may comprise a thread adapted to cooperate with a corresponding thread of the holder so as to allow the holder to be screwed onto the container.

The outlet of the container may be adapted to cooperate with or be defined by a cannula or a needle or a needle hub or an infusion set, or any other fluid communicating conduit adapted to provide fluid access to a medicament accommodated in the container.

The driver of the dosing assembly may comprise a piston rod adapted to move the piston in the distal direction. The piston rod may comprise an element which is more rigid than the piston and is adapted to abut at least a part of and preferably most of the proximal facing surface of the piston whereby a force applied by the piston rod to the rigid element is applied to a larger area of the proximal surface of the piston than if the piston rod had engaged the piston directly.

In the context of the present invention the terms "depression" and "projection" are only used in connection with radially extending members/elements/means, and "indentation" and "protrusion" are only used in connection with axially extending members/elements/means. However, "depression" and "indentation" shall be seen as synonyms and "protrusion" and "projection" shall be seen as synonyms.

The first fastening means may be provided on/by the container or the dosing assembly, and the second fastening means may be provided on/by the dosing assembly. In one embodiment the container comprises the first fastening means and the dosing assembly comprises the second fastening means. In another embodiment the dosing assembly comprises the first fastening means and the container comprises the first fastening means.

In one embodiment the dosing assembly is adapted to encircle at least a part of the container, when the container is fastened to the dosing assembly. As an example a distal end of the dosing assembly may encircle a proximal end of the container. Alternatively, or as a supplement at least a part of the container may be adapted to encircle at least a part of the dosing assembly when the container is fastened to the dosing assembly. In one embodiment the container is received between an inner and an outer wall of the dosing assembly when the container is fastened to the dosing assembly, whereby the outer wall encircles a part of the container, and said part of the container encircles the inner wall of the container.

This paragraph describes a predetermined embodiment. In the embodiment the dosing assembly is adapted to encircle the container when the container is fastened to the dosing assembly. In order to fasten the container to the dosing assembly, a proximal end of the container is inserted into a distal end of the dosing assembly. When the container has reached a predetermined axial position relative to the dosing assembly, the container is rotated relative to the dosing assembly, whereby at least a part of the first fastening means is moved in the radial direction by the second fastening means whereby the container is fastened to the dosing assembly.

It will be appreciated that the principles of the predetermined embodiment also applies to other of the abovementioned configurations e.g. where the container encircles the dosing assembly when the container is fastened to the dosing assembly.

It may be desirable for a user to be able to easily determine when the first and second fastening means are aligned in a predetermined axial position wherein rotation of the container relative to the dosing assembly causes the first fastening to be moved radially by the second fastening means. Thus in one embodiment, the container and/or the dosing assembly may be adapted to indicate to the user when the container has reached or is positioned in said position. This may be achieved by tactile, visible or audio feedback.

In one embodiment a proximal end surface of the container is adapted to abut a distal facing end surface of the dosing assembly (not necessarily the most distal surface) when the container is positioned in said position. In the latter embodiment, the user may insert the container into a cavity of the dosing assembly adapted to receive the container, such that when the container cannot be moved any further axially, relative to the dosing assembly, it is positioned in said predetermined position. Upon subsequent rotation of the container relative to the dosing assembly, the container is fastened to the dosing assembly.

The second fastening means is adapted to move at least a part of the first fastening means in the radial direction upon rotation of the container in the first direction. In one embodiment only tip of the first fastening means is moved in the first radial direction. In another embodiment the majority such as 70% or 80% of the first fastening means is moved in the radial direction during locking/fastening of the container to the dosing assembly.

In one embodiment the container is rotated in the first rotational direction relative to the dosing assembly, when it is rotated clockwise relative to the dosing assembly. In another embodiment the container is rotated counter-clockwise when rotated in the first rotational direction.

When the container is rotated in the first rotational direction, at least a part of the first fastening means may engage at least part of the second fastening means. In one embodiment a proximal facing surface of the second fastening means engage a distal facing surface of the first fastening means, when the container is rotated in the first rotational direction.

A first part of the second fastening means may be adapted to move at least a part of the first fastening means in the radial direction upon rotation of the container in the first rotational direction relative to the dosing assembly, whereby the first fastening means and a second part of the second fastening means engage such that the container and the dosing assembly are locked for relative translational movement.

In order to move the first fastening means radially, at least a part of the first fastening may be bendable or pivotable between an initial non-locking position allowing the container to be inserted into and removed from the dosing assembly, and a retaining or locking position wherein the container, when inserted into the dosing assembly, is retained translationally relative to the container. In the latter case, the second fastening means may be adapted to move the first fastening means into the retaining position upon said rotation of the container in the first rotational direction relative to the dosing assembly. Additionally, when the first fastening means is positioned in the retaining position, rotation of the container in a direction opposite the first rotational direction (relative to the dosing assembly) may cause the first fastening means to be moved from the retaining position into the initial position.

In one embodiment, the first part carrying the first fastening means may include a cylindrical rim part where the rim part comprises an axially extending opening adapted to receive the second fastening means of the second part when the first part is moved axially into engagement with the second part. The rim part further comprises the first fastening means which are formed in a section of said rim part adjoining, in a circumferential direction, said axially extending opening.

The first fastening means may be a segment which is bendable relative to the remainder of the first part and biased towards its initial non-locking position.

In order to bend/pivot the first fastening means into the retaining or locking position, the first fastening means may, upon relative rotation between the container and the dosing assembly, be adapted to bend/pivot about a bending/pivoting axis which is substantially parallel with a longitudinal axis of the medical delivery system. The longitudinal axis may be a centre axis of the container and/or the dosing assembly. Alternatively, the first fastening means may, upon relative rotation between the container and the dosing assembly, be adapted to bend/pivot about a bending/pivoting axis which is substantially parallel with a tangent of a surface of the container and/or the dosing assembly. By 'substantially parallel with a tangent of a surface of the container' is meant that in a predetermined point the first fastening means is bending/pivoting about a tangent of the medical delivery system.

Upon relative rotation between the container and the dosing assembly, the first fastening means is adapted to bend over an angle of at least 10 degrees, such as at least 15 degrees such as at least 20 degrees, such as at least 25 degrees, such as at least 30 degrees, such as at least 45 degrees, such as at least 90 degrees.

In one embodiment only the first fastening means is moved radially upon the relative rotation between the container and the dosing assembly, while the second fastening means remains in essentially the same radial position. In another embodiment both the first and second fastening means are forced in a radial direction upon relative rotation between the container and the dosing assembly. The first and second fastening means may be moved in the same or in opposite radial directions upon said relative rotational movement between the container and the dosing assembly.

In order to force the first and/or second fastening means in the radial direction, at least one of the two may comprise an inclined surface. As an example the second fastening means may comprise an inclined surface which, when the container is rotated relative to the dosing assembly, forces the first fastening means in the radial direction.

The first part carrying the first fastening means may comprise two or more first fastening means adapted to engage a corresponding number of second fastening means of the other part.

In order to ensure that only a predetermined container may be fastened to a predetermined dosing assembly, the first and/or second fastening means may define predetermined coding geometries preventing the container from being fastened to the dosing assembly unless each of the first and/or second fastening means defines a predetermined coding geometry which is selected from a predetermined group of coding geometries. The coding geometry of each of the first and/or second fastening means may be defined by at least one of: a circumferential extent of the fastening means, an axial extent of the fastening means, a radial extent of fastening means and the circumferential position of the fastening means. Alternatively, containers and compatible dosing assemblies may include coding geometries defined by the particular number of corresponding first and second fastening means. Still, in other embodiments, the coding is obtained by the angular distribution of a plurality of first fastening means and corresponding distribution of second fastening means. For example, the spacing of first fastening means may be non-equidistant and the particular spacing pattern be dedicated a specific type of medicament. The number of first and second fastening means may be selected as 2, 3, 4, 5 or even more distinct pairs of fastening means.

One embodiment comprises:
 a first container according to the first aspect of the invention, adapted to be fastened to a first dosing assembly according to the first aspect of the invention; and
 a second container according to the first aspect of the invention, adapted to be fastened to a second dosing assembly according to the first aspect of the invention; and
wherein at least one of the first and/or second fastening means is/are adapted to prevent the first dosing assembly and second container from being fastened to each other, and to prevent the second dosing assembly and the first container from being fastened to each other.

In one embodiment the container comprises a cartridge holder and a cartridge defining said chamber. The second fastening means may be defined by or attached to the cartridge holder.

The cartridge and the cartridge holder may be two separate elements, and the cartridge may be frictionally retained in the cartridge holder. In one embodiment the cartridge is made of glass and the cartridge holder is made of a non-glass material for protecting the glass cartridge. The cartridge may be non-removably retained in the cartridge holder, such that if the cartridge is removed from the cartridge holder it cannot be reattached by hand and without tools. This provides the advantage that the cartridge holder cannot be reused when the cartridge has been emptied, accordingly a cartridge with a wrong medicament cannot be inserted into the cartridge holder and be dispensed by use of the dosing assembly. The cartridge holder and the cartridge may define a monolithic element, i.e. forming one element without seams. Such a monolithic element may be formed as a moulded article made of a synthetic resin such as Topas® or polypropylene. Such a moulded article may include the fastening and coding geometries which are formed during moulding. However, any material which is suitable for long-term storage of the specific medication to be accommodated in the container may be used.

The first and/or second fastening means may define a free end which is connected to the remainder of the container through a connector which is adapted to be broken upon attachment of the container to the dosing assembly, whereby a user can determine that the container has been used previously.

In a SECOND aspect the present invention relates to a container for use in a medical delivery system according to the first aspect of the invention. The container may comprise any combination of features and elements of the first aspect of the invention. As an example it may comprise a fastening means adapted to be moved in radial direction relative to the container between an initial position and a retaining position in which the fastening means extent at least partly away from an outer surface of the container.

When the container defines the first part, the container may include a cylindrical rim part comprising an axially extending opening adapted to receive the second fastening means of the dosing assembly when the container is moved axially into engagement with the dosing assembly. The cylindrical rim part may further comprise the first fastening means which defines a rim segment which is biased towards an initial non-locking position and which is radially moveable away from its non-locking position into the second locking position. The first fastening means defining the rim segment is formed in a section of said rim part adjoining, in a circumferential direction, said axially extending opening.

The first fastening means may define a distally facing locking surface adapted to engage a proximally facing locking surface formed in the dosing assembly. The moveable segment defining the first fastening means may be separated or be separable from adjoining distally located regions of the container, so as to enable the first fastening to be freely moveable in radial direction. The separation may be accomplished by forming a circumferential cut along a part of the first fastening means. Alternatively, the segment forming the first fastening means is connected to distally located regions of the container by a reduced thickness portion adapted to separate or break up upon moving the segment from its initial position into its locking position.

In particular embodiments, the container rim part comprises a plurality of axially extending openings and a plurality of first fastening means, each being formed in a section of said rim part adjoining, in a circumferential direction, a respective axially extending opening.

As described in relation to the first aspect of the invention, the fastening means of the container may be bendable/pivotable about a bending/pivoting axis which is substantially parallel with a longitudinal axis of the container. Additionally the fastening means of the container may be bendable/pivotable about a bending/pivoting axis which is substantially parallel with a tangent of an outer surface of the container.

Moreover, the fastening means may define a free end which is connected to the remainder of the container through a connector which is adapted to be broken upon attachment of the container to a dosing assembly of the medical delivery system according to the first aspect of the invention, whereby a user can determine that the container has been used previously.

In a THIRD aspect the present invention relates to a dosing assembly for use in the medical delivery system according to the first aspect of the invention. The dosing assembly may comprise any combination of features and elements of the first aspect of the invention.

BRIEF DESCRIPTION OF THE FIGURES

The invention will now be described with reference to the drawings in which:

FIGS. 1 and 2 disclose an isometric and sectional view of a part of a dosing assembly of a first embodiment of the invention, FIGS. 3a and 4 disclose an isometric and sectional view of a part of a dosing assembly of a second embodiment of the invention, FIG. 3b shows an alternative to the second embodiment, FIG. 5 discloses a first container for use in the first and second embodiment, FIG. 6 discloses a second container according to a third embodiment of the invention, FIGS. 7-9 disclose sections of a fourth embodiment of the invention, FIGS. 10-16 disclose different embodiments of the first fastening means, and FIGS. 17-21 disclose an alternative to the fourth embodiment wherein the inner member is axially movable relative to the outer member.

DETAILED DESCRIPTION OF THE FIGURES

Figure 7:
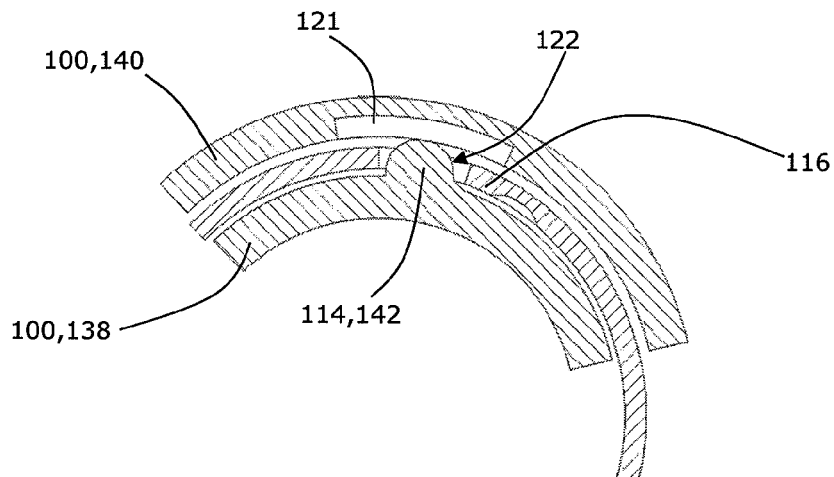

FIGS. 1 and 2 disclose a first embodiment of a part of a dosing assembly 100 of a medical delivery system 102 according to the invention. The dosing assembly 100 and the container 104 a part of which is disclosed in FIG. 5, are adapted to be connected to each other by inserting the proximal end 106 of the container 104 into an opening 108 defined in a distal end 110 of the dosing assembly 100. Such insertion causes an end surface 107 of the proximal end 106 of the container 104 to abut a distal facing inner surface 112 of the dosing assembly 100 whereby further axial movement of the container 104 in the proximal direction (relative to the dosing assembly 100) is prevented.

The container 104 comprises first fastening means 116 which in the shown embodiment is formed in a proximal rim section of the container. Adjacent the first fastening means 116 in the direction of circumference is an axial extending indentation or opening. The dosing assembly 100 comprises second fastening means 114 in the form of an axially extending protrusion. When the container axially approaches the dosing assembly, the second fastening means 114 may be aligned with the axial extending indentation or opening formed in the container 104 and introduced therein so that the second fastening means 114 is positioned adjacent the first fastening means.

Upon clockwise rotation of the container 104 relative to the dosing assembly 100 the second fastening means 114 of the dosing assembly 100 causes the first fastening means 116 of the container 104 to be moved radially outwards relative to a centre axis 118 of the container 104 and into a retaining or locked position, disclosed in FIG. 5. Accordingly, each of the first fastening means 116 is adapted to be moved between a retaining position (disclosed in FIGS. 5, 6, 8, 9, 10 and 12) and an initial position (disclosed in FIGS. 7, 11, 13, 14, 15 and 16).

The radially outwards movement of the first fastening means 116 is caused by engagement between a first inclined surface 120 (see FIGS. 10-13) of the first fastening means 116 and a second inclined surface 122 (see FIGS. 10-12) of the second fastening means 114. Upon the clockwise rotation of the container 104 relative to the dosing assembly 100, the first inclined surface 120 will slide onto the second inclined surface 122 which will cause the first fastening means 116 to be moved radially. In the embodiment of FIG. 1-4 the second fastening means 114 is substantially non-bendable in the radial direction, and thus, any rotational movement between the first fastening means 116 and the second fastening means 114 cases the first fastening means 116 to be moved radially outwards, while the second fastening means 114 remains in substantially the same radial position. In other embodiments, the first and second fastening means 116,114 are moved in opposite radial directions, as is described below in relation to FIG. 12.

In order to provide a substantially non-bendable second fastening means 114, at least a part of the second fastening means 114 may be attached to or integrated with an inner sidewall 124 of the dosing assembly 100, as disclosed in FIGS. 1 and 2. Alternatively, the second fastening means 114 may define a free end 126 which is not attached to or integrated with the inner sidewall 124, as disclosed in FIGS. 3a and 4. FIG. 3b discloses an alternative to the embodiment of FIGS. 3a and 4. In FIG. 3b an end wall 115 of the second fastening means 114 is connected to an inner sidewall 124 of the dosing assembly 100 in order to strengthen the second fastening means 114.

When the first fastening means 116 is in the retaining position a distal facing surface 128 of the first fastening means 116 will abut a proximal facing surface 130 of the second fastening means 114, whereby the container 104 is locked for axial movement relative to the dosing assembly 100. In some embodiments the first fastening means 116 may be movable between a position where in the distal facing surface 128 abuts the proximal facing surface 130 and a position wherein the two surfaces do not abut.

It will be appreciated that upon anticlockwise rotation of the container 104 relative to the dosing assembly 100 the first fastening means 116 is moved from the retaining position and into the initial position whereby the container 104 may be moved axially out of the dosing assembly 100.

In the embodiment of FIG. 5, the first fastening means 116 is adapted to be bent about a bending axis 132 which is substantially parallel with a centre axis 118 of the container 104. In an alternative embodiment disclosed in FIG. 6, the first fastening means 116 is adapted to be bend about a bending axis 134 which in at least one point, is substantially parallel with a tangent to an outer surface 136 of the container 104. In order to retain the first fastening means 116 relative to the dosing assembly 100, the latter may define a wedge-shaped indentation into which the first fastening means 116 is moved upon relative rotation between the dosing assembly 100 and the container 104. Accordingly, application of a torque by the user to the container 104 (relative to the dosing assembly 100) causes the first fastening means 116 to be wedged into the wedge-shaped indentation, whereby the container 104 is retained axially relative to the dosing assembly 100.

Figure 8:
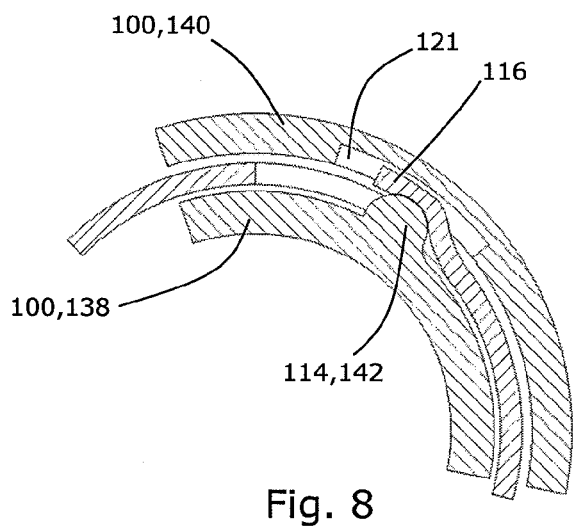
Figure 9:
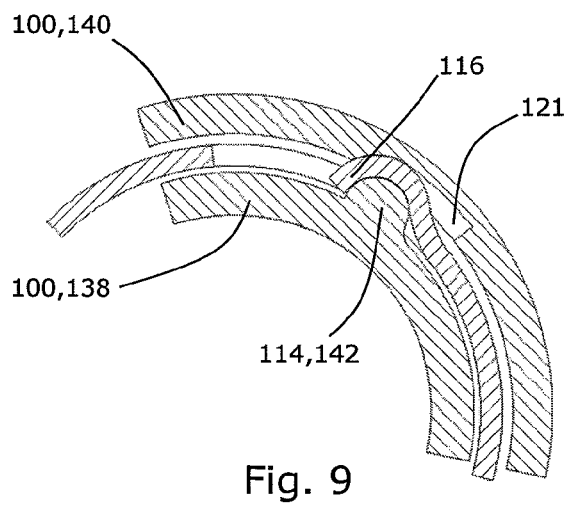

FIGS. 7-9 disclose a fourth embodiment of the invention wherein the dosing assembly 100 defines two concentric ring-shaped members, an inner member 138 and an outer member 140. The second fastening means 114 is defined by a knob 142 on the inner member 138. During insertion of the container 104 into the dosing assembly 100 the container 104 is inserted between the inner member 138 and the outer member 140, whereby rotation of the container 104 in a counter clockwise direction relative the dosing assembly 100 causes the first fastening means 116 to abut a second inclined surface 122 of the knob 142. Upon further relative rotation the first fastening means 116 is forced radially outwards as disclosed in FIGS. 8 and 9, whereby the container 104 is locked axially relative to the dosing assembly 100 as described above in relation to FIGS. 1-4.

Figure 10:
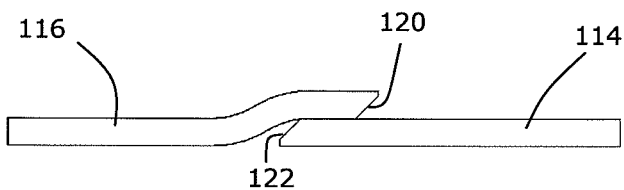
Figure 11:
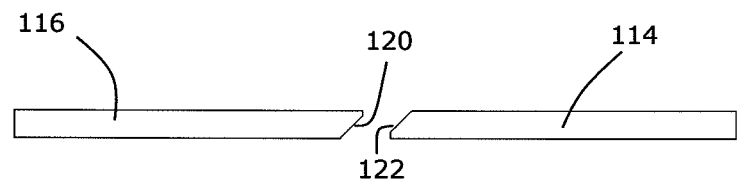
Figure 12:
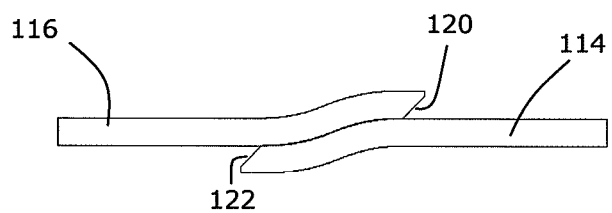

FIGS. 10 to 12 disclose two embodiments of the first and second fastening means 116,114. In an initial position disclosed in FIG. 11 the first fastening means 116 does not engage the second fastening means 114. When the first and second fastening means 116,114 are moved towards each other the first and/or the second fastening means 116,114 is/are moved in a radially away from the initial position and into a retaining position. In FIG. 10 only the first fastening means 116 is moved away from the initial position while the second fastening means 114 maintains its position as the second fastening means 114 is more rigid than the first fastening means 116. In FIG. 12 both the first and second fastening means 116,114 are moved away from their initial positions. Due to the first inclined surface 120 and the second inclined surface 122, movement of the first and second fastening means 116,114 towards each other will cause the first and/or second fastening means to be moved away from its/their the initial position(s).

Figure 13:
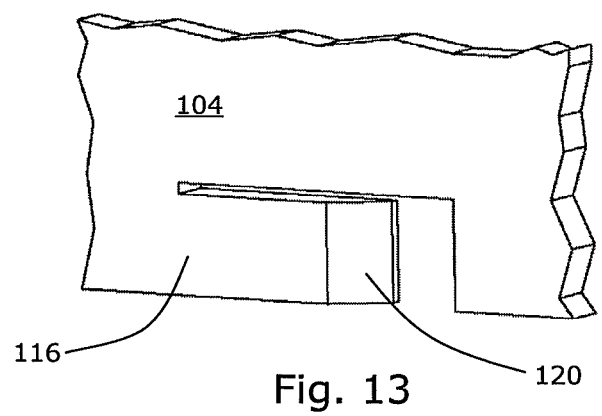
Figure 14:
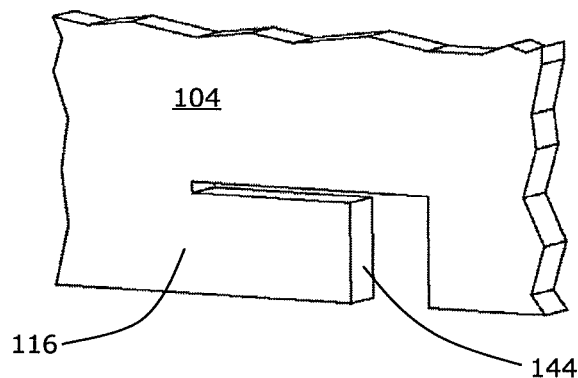
Figure 15:
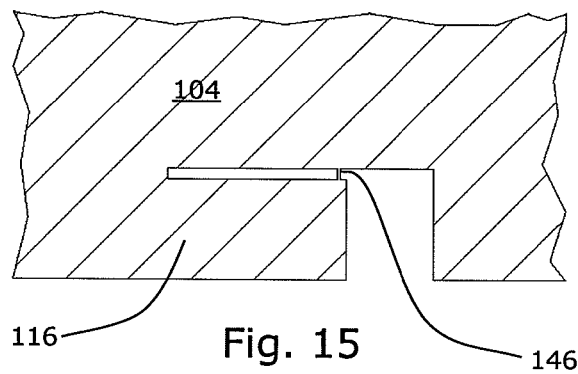
Figure 16:
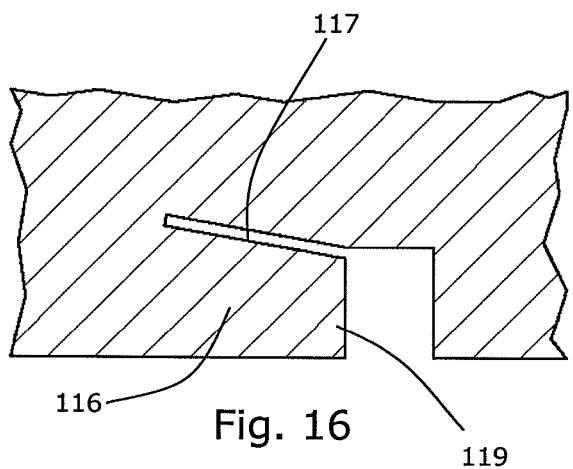

FIGS. 13-16 disclose different embodiments of the first fastening means 116. In FIG. 13 the first fastening means 116 defines a first inclined surface 120 as described in the aforementioned, whereas the first fastening means 116 of FIGS. 14 and 15, do not comprise the inclined surface. Instead the first fastening means 116 of FIGS. 14 and 15 define a flat end surface 144. In the embodiment of FIG. 15 the first fastening means 116 is connected to the remainder of the container 104 by means of connector 146 which retain the first fastening means 116 in the initial position prior to the first use of the container 104. Upon fastening of the container 104 to a dosing assembly 100, the first fastening means 116 is moved into the retaining position whereby the connector 146 is broken. This enables a user to see whether the container 104 has been used or at least been fastened to a dosing assembly previously. FIG. 16 discloses a wedge-shaped first fastening means 116 defining an inclined surface 117. When the tip 119 of the first fastening means 116 is received in the second fastening means, rotation of the container relative to the dosing assembly 100 causes the container to be moved axially in the proximal direction relative to the dosing assembly due to the engagement between the second fastening means and the inclined surface 117.

Figure 17:
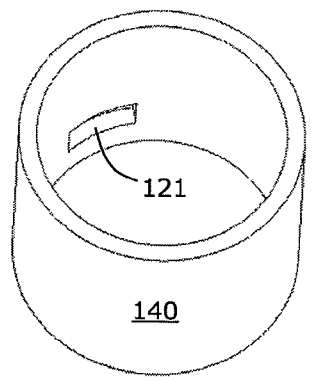
Figure 18:
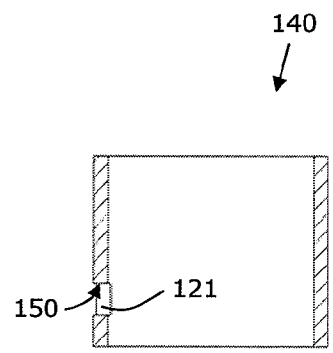
Figure 19:
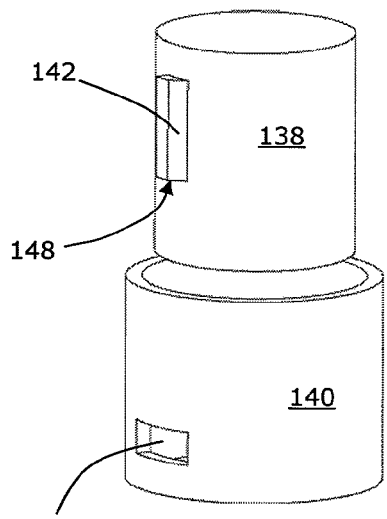

FIGS. 17-21 disclose an alternative to the embodiments of FIG. 7-9. In the embodiment of FIGS. 17-21 the inner member 138 and the outer member 140 are defined by two separate elements which are axially (and/or rotationally) movable relative to each other. FIGS. 17 and 18 disclose an isometric and a sectional view of the outer member 140, respectively. The outer member 140 defines an indentation 121 for receiving the first fastening means 116 as described in relation to FIGS. 7-9. The inner member 138 defines a knob 142 for moving the first fastening means 116 into the indentation 121, depending on the axial position of the inner member 138 relative to the outer member 140.

Figure 20:
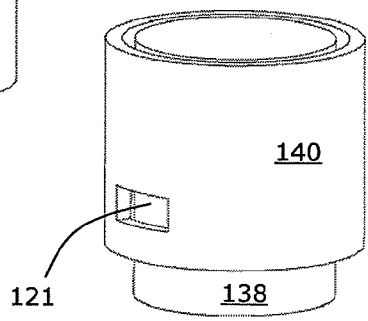

When the inner member 138 is positioned in the distal position as disclosed in FIG. 20, the knob 142 and the indentation 121 are positioned in two different axial positions, such that a proximal end surface 148 of the knob 142 is distal relative to a proximal wall 150 of the indentation 121. Accordingly, rotation of the container (not shown) relative to the dosing assembly 100 will not cause the first fastening means 116 to be moved into the indentation 121, as the knob 142 and the indentation 121 are not axially aligned.

Figure 21:
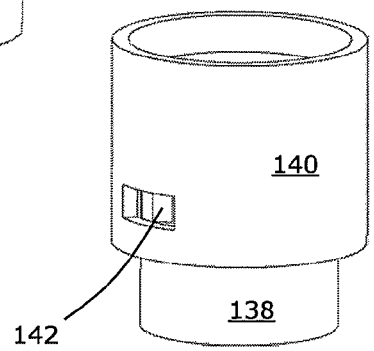

FIG. 21 discloses the inner member 138 positioned in a proximal position relative to the outer member 140, wherein at least a part of the indentation 121 and the knob 142 are positioned in the same axial position, whereby rotation of the container (not shown) relative to the dosing assembly 100 causes the first fastening means 116 to be moved into the indentation 121 as described in connection with FIG. 7-9.

In the embodiment of FIGS. 17-21, the container 104 may comprise a cartridge holder and a glass cartridge defining the chamber of the container. The glass cartridge may be designed to abut the inner member 138 when the container 104 is fastened to the dosing assembly 100, whereby axial movement of the container 104 (and thus the glass cartridge) during fastening causes the inner member 138 to be moved into the proximal position and thus allowing the first fastening means 116 to be moved into the indentation 121.

The invention claimed is:

1. A medical delivery system comprising:
    a container adapted to contain a medicament in a chamber;
    a dosing assembly adapted to be fastened to the container;
    wherein one of the container and the dosing assembly defines a first part comprising a first fastening means and the other one of the container and the dosing assembly defines a second part comprising a second fastening means, the first fastening means and the second fastening means being adapted to fasten said first part to the second part by translationally moving the first part relative to the second part along the center axis followed by a relative rotational locking movement around the center axis;
    wherein the first part includes a cylindrical rim part, the rim part comprising an axially extending opening adapted to receive the second fastening means of the second part when the first part is moved along the centre axis into engagement with the second part,
    wherein the rim part further comprises the first fastening means which are formed in a section of said rim part adjoining, in a circumferential direction, said axially extending opening;
    wherein the first fastening means is radially moveable from an initial non-locking position into a second locking position by bending or pivoting about a bending axis which is substantially parallel with the center axis, the first fastening means further defining a first locking surface adapted to engage a second locking surface formed in the second part when the first fastening means is in its second locking position whereby the first part is axially retained with respect to the second part; and
    wherein, responsive to said relative rotational locking movement, the second fastening means urges the first fastening means into its second locking position upon relative rotational movement between the first fastening means and the second fastening means.

2. A medical delivery system according to claim 1, wherein, when the first fastening means is positioned in the second locking position such that the first part is retained axially relative to the second part, relative rotation in a direction counter to said relative rotational locking movement, causes the first fastening means to be moved into its initial non-locking position.

3. A medical delivery system according to claim 1, wherein the first fastening means is a segment which is bendable relative to the remainder of the first part and biased towards its initial non-locking position.

4. A medical delivery system according to claim 1, wherein both the first fastening means and second fastening means are forced in a radial direction upon relative rotation between the first part and the second part.

5. A medical delivery system according to claim 1, wherein the second fastening means comprises an inclined surface which, when the first part is rotated relative to the second part, forces the first fastening means in the radial direction.

6. A medical delivery system according to claim 1, wherein the first part comprise a plurality of first fastening means and wherein the second part comprise a corresponding plurality of second fastening means.

7. A medical delivery system according to claim 1, wherein the first fastening means and/or the second fastening means define(s) predetermined coding geometries preventing the container from being fastened to the dosing assembly unless each of the first and/or second fastening means defines a predetermined coding geometry which is selected from a predetermined group of coding geometries.

8. A medical delivery system according to claim 7, wherein the coding geometry of each of the first and/or second fastening means is defined by at least one of: a circumferential extent of the fastening means, an axial extent of the fastening means, a radial extent of fastening means and the circumferential position of the fastening means.

9. A medical delivery system according to claim 1, comprising:
    a first container according to any of the preceding claims adapted to be fastened to a first dosing assembly according to any of the preceding claims; and
    a second container according to any of the preceding claims adapted to be fastened to a second dosing assembly according to any of the preceding claims; and
    wherein at least one of the first fastening means and/or the second fastening means is/are adapted to prevent the first dosing assembly and second container from being fastened to each other, and to prevent the second dosing assembly and the first container from being fastened to each other.

* * * * *

UNITED STATES PATENT AND TRADEMARK OFFICE
CERTIFICATE OF CORRECTION

PATENT NO. : 8,617,125 B2  
APPLICATION NO. : 12/517896  
DATED : December 31, 2013  
INVENTOR(S) : Asger Voss Christiansen It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 783 days.

Signed and Sealed this
Eleventh Day of August, 2015

Michelle K. Lee
*Director of the United States Patent and Trademark Office*